United States Patent [19]

Green et al.

[11] 4,444,750
[45] Apr. 24, 1984

[54] METHOD OF CONDITIONING HAIR

[75] Inventors: Harold A. Green, Havertown, Pa.; John J. Merianos, Middletown; Alfonso N. Petrocci, Glen Rock, both of N.J.

[73] Assignee: Millmaster Onyx Group, Inc., New York, N.Y.

[21] Appl. No.: 390,296

[22] Filed: Jun. 21, 1982

Related U.S. Application Data

[60] Division of Ser. No. 206,997, Nov. 17, 1980, Pat. No. 4,374,244, Continuation-in-part of Ser. No. 29,778, Apr. 13, 1979, Pat. No. 4,304,910, Continuation-in-part of Ser. No. 902,894, May 4, 1978, Pat. No. 4,190,644, Continuation-in-part of Ser. No. 744,617, Nov. 24, 1976, Pat. No. 4,089,977.

[51] Int. Cl.$^3$ .................................................. A61K 7/06
[52] U.S. Cl. ..................................... 424/70; 424/329
[58] Field of Search ............................................ 424/70

[56] References Cited

U.S. PATENT DOCUMENTS 3,931,319 1/1976 Green et al. ...................... 564/295
3,966,904 6/1976 Green et al. ...................... 564/295
4,027,020 5/1977 Green et al. ...................... 564/295
4,197,865 4/1980 Jacquet et al. .................... 564/292
4,304,910 1/1981 Green et al. ...................... 544/87

Primary Examiner—Dale R. Ore
Attorney, Agent, or Firm—Arthur A. Jacobs

[57] ABSTRACT

A method of conditioning hair by applying thereto a quaternary ammonium polymers having formula

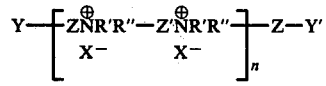

wherein R' and R" may be the same or different alkyl groups of from 1 to 18 carbon atoms, optionally substituted by from 1 to 2 hydroxyl groups or, when taken together, with N form a saturated or unsaturated ring of from 5 to 7 atoms, or when taken together with N and an oxygen atom form the N-morpholino group; wherein Z is $-CH_2CH=CHCH_2-$ when Z' is $-CH_2CHOHCH_2-$ or Z is $-CH_2CHOHCH_2-$ when Z' is $-CH_2CH=CHCH_2-$; wherein X is a halogen of atomic weight greater than 30; wherein Y and Y' may be either the same or different and may be either X or $-NR'R''$; and wherein n is an integer of from 2 to 20.

9 Claims, No Drawings

METHOD OF CONDITIONING HAIR

This is a division of Application Ser. No. 206,997, filed Nov. 17, 1980, now issued as U.S. Pat. No. 4,374,244, dated Feb. 15, 1983, the latter being a continuation-in-part of Application Ser. No. 29,778, filed Apr. 13, 1979 now issued as U.S. Pat. No. 4,304,910, dated Dec. 8, 1981 which is, in turn, a continuation-in-part of Application Ser. No. 902,894, filed May 4, 1978 and issued as U.S. Pat. No. 4,190,644, dated Feb. 26, 1980, and that, in turn, was a continuation-in-part of Application Ser. No. 744,617, filed Nov. 24, 1976 and issued as U.S. Pat. No. 4,089,977 on May 16, 1978. The disclosures of these prior applications are incorporated herein by reference.

PRIOR ART

A. U.S. Pat. Nos. 3,874,870, 3,923,973, 3,929,990, 3,931,319, 3,933,812, 3,961,042, 4,001,432, 4,005,193, 4,012,446, 4,025,617, 4,025,653, 4,026,945, 4,027,020, 4,035,480, 4,036,959, 4,055,712, and 4,091,113, all of which, as a group, disclose the preparation and properties of linear polymeric quaternary ammonium compounds with repeating unit

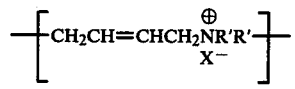

B. The aforementioned Application Ser. No. 29,778, U.S. Pat. Nos. 4,089,977 and 4,190,644, as well as U.S. Pat. Nos. 4,140,798 and 4,188,293, all, as a group, disclose the preparation and properties of linear polymeric quaternary ammonium compounds with repeating unit

The aforesaid prior art polymeric were synthesized by causing approximately equimolar quantities of monomers X—Z—X and R'R" N—ZNR'R" to react, forming polymeric products that may be represented by the formula

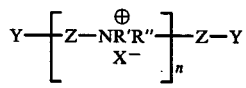

where Z is either —CH$_2$CH=CHCH$_2$— or —CH$_2$CHOHCH$_2$—, Y is either X or —NR'R", X is a halogen of atomic weight greater than 30, n is an integer of from 2 to 20, and R' and R" (I) may be the same or different alkyl groups of from 1 to 18 carbon atoms optionally substituted by from 1 to 2 hydroxyl groups; or (II) when taken together with N represents a saturated or unsaturated ring of from 5 to 7 atoms; or (III) when taken together with N and an oxygen atom represent the N-morpholino group.

The prior art listed above also disclosed two methods of "capping" these polymers by placing quaternary ammonium groups at the two chain termini, thereby preventing the polymeric chain from propogating by way of engaging in a quaternizing reaction. The "capped" polymers may be represented by the formula

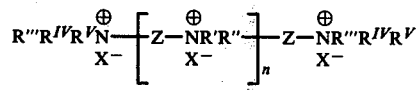

where (I) R''', R$^{IV}$ and R$^V$ may be the same or different alkyl groups of from 1 to 18 carbon atoms optionally substituted by from 1 to 2 hydroxyl groups, or (II) R''' is a lower alkyl group of from 1 to 4 carbon atoms and R$^{IV}$ and R$^V$ taken together with N represent a saturated or unsaturated heterocyclic ring of from 5 to 7 atoms; or (III) R''' is a lower alkyl group of from 1 to 4 carbon atom sand R$^{IV}$ and R$^V$ taken together with N and an oxygen atom represent the N-morpholino group; and the other symbols R', R", Z, n and x have the same meaning given to them previously.

DESCRIPTION OF INVENTION

A new system of linear polymeric quaternary ammonium materials has been discovered which, as a group, has antimicrobial properties generally at least as effective as those previously prepared and described above, and, in addition, has cosmetic properties, especially hair care properties, that are superior to the prior art compounds.

These new polymers may be represented by the formula

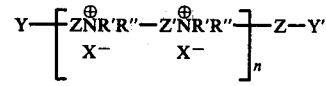

where Z is —CH$_2$CH=CHCH$_2$— when Z' is —CH$_2$CHOHCH$_2$—, or Z is —CH$_2$CHOHCH$_2$— when Z' is —CH$_2$CH=CHCH$_2$—, Y and Y' may be the same or different, and either X or —NR'R", all the other symbols retaining the same meanings as given above.

Close inspection of the molecular formulas of the prior art and of the present invention will reveal that the prior art polymers have only one repeating unit along the linear chain, either

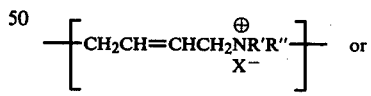

or

but the present invention contains both of these units alternately bonded to each other along the linear polymeric chain so that the real repeating unit of the invention, as disclosed in the formula, is either

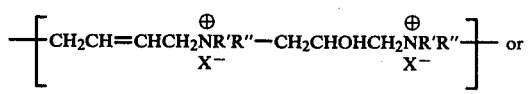 or

-continued

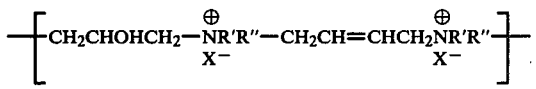

The origin of two possible repeating units in the molecular formula can be found in the method of synthesis.

The new polymers may be made either from $$XCH_2CH=CHCH_2X + R'R''NCH_2CHOHCH_2NR'R'',$$

or from $$XCH_2CHOHCH_2X + R'R''NCH_2CH=CHCH_2NR'R''$$

where X, R', and R'' have the same meanings given above.
Thus, to illustrate by specific examples:

$$ClCH_2CH=CHCH_2Cl + (HOCH_2CH_2)_2NCH_2CHOHCH_2N(CH_2OH_2CH)_2 \longrightarrow$$

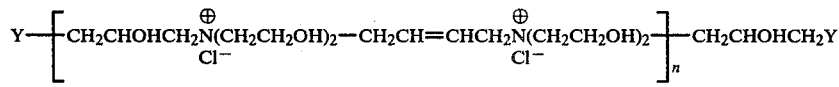

where Y is either —N(CH$_2$CH$_2$OH)$_2$ or

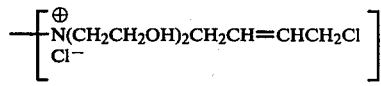

and $$N(CH_2CH_2OH)_2CH_2=CHCH_2N(CH_2CH_2OH)_2 + ClCH_2CHOHCH_2Cl \longrightarrow$$

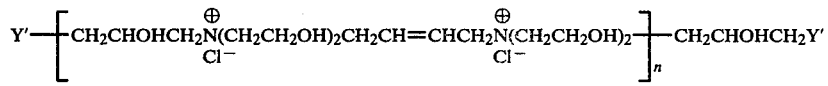

where Y' is either —Cl or

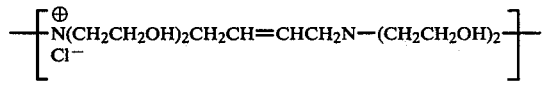

In the manner common to the writing of polymerization equations, the equations above are not balanced lest the plethora of stochiometric details mask the similarities and differences of the methods they describe.

The capped quaternary ammonium polymers of the present invention may be represented by two different molecular formulas. The proper molecular formula depends on which monomers are used to make the polymer.

When the monomers are XCH$_2$CH=CHCH$_2$X and R'R''NCH$_2$CHOHCH$_2$NR'R'', the capped product may be represented by the molecular formula

But when the monomers are XCH$_2$CHOHCH$_2$X and R'R''NCH$_2$NR'R'', the capped polymeric product may be represented by the molecular formula

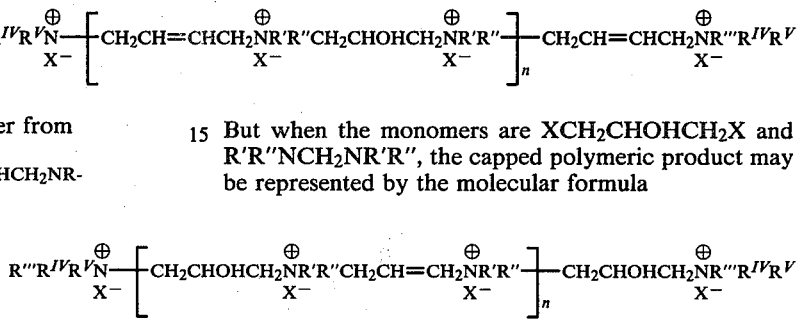

where R''', R$^{IV}$ and R$^V$ have the same meaning they had in the capped polymers compounds of the prior art, and R', R'', n and X have the same meanings as those given above.

The capped derivatives of the quaternary ammonium polymers of this invention may be made by the two methods not unlike the methods described in the prior art.

In the first method a compound of the type R'R''N—Z—NR'R'' is made to react with a molar excess of a compound of the type X—Z'—X, thereby leading to polymers of formula

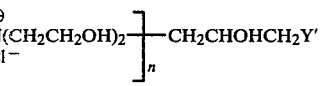

where Z is —CH$_2$CH=CHCH$_2$— when Z' is —CH$_2$CHOHCH$_2$—, and Z is —CH$_2$CHOHCH$_2$— when Z' is —CH$_2$—CH=CHCH$_2$—. After divesting the mother liquors of unreacted starting monomers, the residue is quaternized by adding a calculated quantity of NR'''R$^{IV}$R$^V$ in a second reaction. All symbols retain their prior meanings as disclosed above. Thus, as a specific example, $$(CH_3)_2NCH_2CH=CHCH_2N(CH_3)_2 + \text{a molar excess of } ClCH_2CHOHCH_2Cl \longrightarrow$$

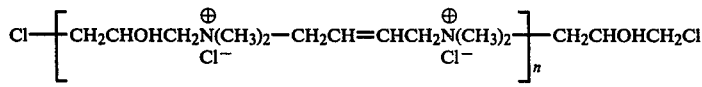

Reacting the above product with a calculated amount of

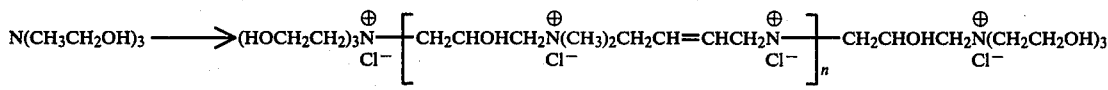

If (CH₃)NCH₂CHOHCH₂(CH₃)₂ and ClCH₂CH=CHCH₂Cl were the starting monomers, the formula for the capped polymer would be It has been found that the preferred molar ratio of bis-3° amine monomer to mono-3° amine molecule is 10:1. The two extreme acceptable ratios are 20:1 and 2:1. A ratio outside this range will produce products with at least one of its properties inferior.

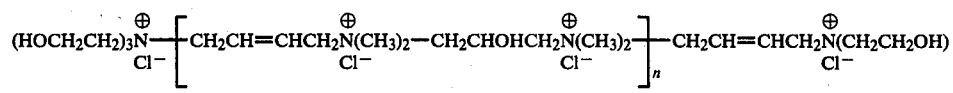

The method of preparing capped polymers described above is not the preferred method because it involves two separate steps, first making the polymer with halogen termini, then capping the termini with a 3° amine.

The second method of making the capped polymers of this invention is the preferred method because it involves only a single operation. In this method, a monomer of formula X—Z—X is made to react with the monomer R'R''N—Z'NR'R'' in the presence of a tertiary amine RN'''R$^{IV}$R$^V$ in ratios such that the sum of the tertiary amino equivalents in the di-amino monomer, and mono-amine, is approximately equal to the sum of the halogen equivalents in the di-halo monomer, and the number of moles of di-amino monomer is at least twice the number of moles of monoamine. This single reaction leads directly to the capped polymers of this invention.

The principle of the one reaction procedure is as follows: When a di-halo monomer reacts with one amino group of the di-amino monomer, it creates a molecule with a halogen terminus. This halogen terminus may react with either a di-amino monomer or a tertiary amine molecule. When it reacts with the di-amino monomer, a molecule with two tertiary amino termini is created. When it reacts with the mono tertiary amine, a quaternary ammonium terminus is created. Since the quaternized terminus may no longer react with a monomer to extend the chain, the quaternary terminus has "capped" this end of the molecule.

Whatever is true during the early stages of chain propogation also pertains during the later stages of chain propogation. Thus, for chain propogation to occur, a 3° amino terminus must react with a di-halo monomer, thereby producing a halogen terminus. The halogen terminus must react with a bis-3° amino terminus, for chain propogation. But, if the halogen terminus reacts with a mono-tertiary amine molecule, a quaternary ammonium terminus is produced and the molecule becomes "capped" at the end.

The average molecular weight of the polymer depends, to a large extent, on the molar ratio of di-tertiary amino monomer to mono-tertiary amine molecule. But, a sufficient number of mono-tertiary amino molecules must be present if the main product is to be "capped".

Since the "capping" reaction is random, the range of molecular weights in the product may be expected to be wider than in the two-reaction procedure where polymerization runs its course before the capping.

The preferred one-reaction procedure was used almost exclusively in the preparation of polymers of this invention. Only one two-step synthesis was performed, mainly for the purpose of showing that this synthesis was feasible. The "same" polymeric products made by the one-step and two-step methods were chemically indistinguishable from each other by simple methods, and had identical anti-microbial and cosmetic properties.

The formula for the divalent 2-butene-1,4-diyl chain (—CH₂CH=CHCH₂—) represents both the cis and trans possibilities of this group, and also, what is most likely from a practical point of view, mixtures of these two steric possibilities.

The specific products prepared and tested were synthesized from a 5% cis:95% trans mixture of 1,4-dichloro-2-butene, and also repeated with a 30% cis:70% trans mixture of the monomer.

The 1,4-di-3° amino-2-butene monomers were made from each of the 1,4-dichloro-2-butene isomer mixtures disclosed above by causing them to react with 2° amines. No effort was made to determine whether the cis:trans ratio of the dichlorobutene was changed during the amination.

Since there were no observable differences in the anti-microbial effectiveness or the hair-care properties in the two sets of products made from monomers originating from starting materials with different cis:trans ratios, it was presumed that the steric differences of the products, due to different cis:trans ratios of the 2-butene group, does not alter the practical usefulness of the polymers.

In principle, a significant variance in this ratio might affect the average molecular weight of the product, and perhaps other properties, but this matter was not investigated.

Some of the reactions were repeated several times, each in a different solvent. The solvents were water, methanol, 95% ethanol, isopropanol and a 50:50 mixture by weight of water and isopropanol.

All the polymers were soluble in water, methanol and 95% ethanol, the product being a viscous solution containing about 30%-50% active solids. Sometimes the 95% ethanol solution deposited a little solid upon long standing, but the solid dissolved when a little water was added. Isopropanol solvent did not dissolve the product. The insoluble polymer was filtered out and dissolved in water. The anti-microbial and hair-care properties of this aqueous solution were identical to those of the similar product made in water. However, when a 50:50 mixture by weight of isopropanol and water was used as the reaction solvent, a clear viscous solution was the product.

The products of this invention, therefore, appear to be soluble in water, methanol, 95% ethanol, and 50:50 isopropanol-water by weight, and insoluble in pure isopropanol.

The following examples illustrate more clearly the procedural details of making the compounds of this invention.

EXAMPLE 1

142 grams (1 mole) of 1,4-bis-(dimethylamino)-2-butene ($R'=R''=-CH_3$) made from 1,4-dichloro-2-butene, 5% cis, 95% trans; and 129 grams (1 mole) of 1,3-dichloro-2-propanol and 500 grams of water were mixed thoroughly while heated to 80°-90° C. on a steam bath, and kept at that temperature with constant stirring for 6 hours. Analysis of the homogeneous viscous reaction product for ionic chloride indicated that the reaction was about 98% complete. The viscous liquid was subjected to steam distillation to remove volatile material, namely unreacted monomer. The residue contained about 35% active solids, and was used 'as is' for testing.

The reaction was repeated, except that methanol, 95% ethanol, isopropanol and 50:50 mixture by weight of isopropanol and water were used as solvents in separate reactions, instead of water. All products were homogeneous viscous solutions except for the product made in isopropanol. In isopropanol the reaction mixture began to deposit solid polymer shortly after the reaction commenced. The solid product was filtered off, dissolved in water, and the aqueous solution used for testing.

EXAMPLE 2

The procedures disclosed in Example 1 were repeated, except that the 1,4-bis-(dimethylamino)-2-butene was prepared from 1,4-dichloro-2-butene which was about 30% cis, and about 70% trans. There were no apparent differences between these products and the products synthesized in Example 1.

EXAMPLE 3

The procedures of Example 1 were followed, except that 1 mole of 1,4-bis-(di-(2-hydroxyethlamino)-2-butene ($R'=R''=-CH_2CH_2OH$) was used instead of the 1,4-bis-(dimethylamino)-2-butene.

EXAMPLE 4

The procedure of Example 2 was followed, except that 1 mole of 1,4-bis-(di-(2-hydroxyethylamino)-2-butene ($R'=R''=-CH_2CH_2OH$) was used instead of the 1,4-bis-(dimethylamino)-2-butene.

EXAMPLE 5

The procedure of Example 1 was used, using water only as a solvent, for the bis amines in which:

(a) $R'=-C_{12}H_{25}$ and $R''=-CH_3$

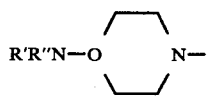
(b)

EXAMPLE 6

125 grams (1 mole) of 1,4-dichloro-2-butene (5% cis, 95% trans) and 146 grams (1 mole) of 1,3-bis-(dimethylamino)-2-propanol and 500 grams of water were mixed thoroughly while heated on a steam bath to 80°-90° C., and kept at that temperature with constant stirring for 6 hours. Analysis of the reaction product for ionic chloride indicated that the reaction was about 98% complete. The viscous liquid was subjected to steam distillation to remove volatile materials, namely unreacted monomers. The residue contained about 35% active solids, and was used 'as is' for testing.

The reaction was repeated except that methanol, ethanol and a 50:50 mixture by weight of isopropanol and water were used as solvents, in separate reactions, instead of water. All products were homogeneous viscous liquids containing about 35% active solids.

When the reaction was repeated using pure isopropanol as solvent, the reaction product was a solid. The solid was filtered off, dried, dissolved in water to known concentrations, and the aqueous solution used for testing.

EXAMPLE 7

The procedures disclosed in Example 6 were repeated, except that the 1,4-dichloro-2-butene was a mixture of about 30% cis and about 70% trans.

EXAMPLE 8

The procedures of Example 6 were followed except that 1 mole of 1,3-bis-[(di-(2-hydroxyethylamino)-2-propanol was used instead of 1,3-bis-(dimethylamino]-2-propanol.

EXAMPLE 9

The procedures of Example 7 were followed except that 1 mole of 1,3-bis-[(di-(2-hydroxyethylamino)]-2-propanol was used instead of 1,3-bis-(dimethylamino)-2-propanol.

EXAMPLE 10

The procedure of Example 6 was followed using water only as a solvent, for the bis-amines in which (a) $R'=-C_{12}H_{25}$ and $R'=-CH_3$

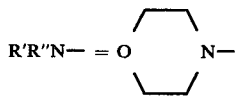
(b)

EXAMPLE 11

142 grams (1 mole) of 1,4-bis-(dimethylamino)-2-butene (made from 1,4-dichloro-2-butene, 5% cis, 95% trans) and 142 grams (1.1 moles) of 1,3-dichloro-2- propanol and 500 grams of water were mixed thoroughly while heated at 80°–90° C., and kept at that temperature, with constant stirring, for 6 hours. After cooling, the unreacted monomers were extracted with ether. The difference between analyses for total chloride and ionic chloride indicated that 0.11 mole of terminal chloride was present. An aqueous solution containing 0.11 mole of trimethyl amine was added and the mixture stirred for 1 hour at room temperature, and 2 hours at 80°–90° C., and then cooled. The viscous liquid had the same properties as the product made in Example 12.

EXAMPLE 12

128 grams (0.9 mole) of 1,4-bis-(dimethylamino)-2-butene (made from 5% cis, 95% trans, 1,4-dichloro-2-butene), and 129 grams (1.0 mole) of 1,3-dichloro-2-propanol, and 30 grams (0.2 mole) of triethanolamine, and 600 grams of water were mixed while heated on a steam bath to 80°–90° C., and kept at that temperature for 6 hours with constant stirring. Analysis of the viscous liquid product for ionic chloride indicated that the reaction was about 98% complete. It contained about 33% active solids.

Half of the product was subjected to steam distillation for the purpose of removing any unreacted monomers or other volatile matter, but the residue appeared to be identical to the undistilled portion.

EXAMPLE 13

The procedure of Example 12 was repeated, except that the 1,4-bis-(dimethylamino)-2-butene was made from 30% cis, 70% trans, 1,4-dichloro-2-butene. The product appeared to have identical properties to the product of example 12.

EXAMPLE 14

The procedure of Example 13 was repeated, except that the monoamine used was trimethylamine.

EXAMPLE 15

The procedure of Example 13 was repeated except that the monoamine used was docecyl dimethylamine ($R''' = C_{12}H_{25}$; $R^{IV} = -CH_3$; $R^V = -CH_3$)

EXAMPLE 16

The procedure of Example 13 was repeated, except the monoamine used was N-methyl morpholine

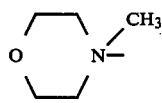

EXAMPLE 17

131 grams (0.9 mole) of 1,3-bis-(dimethylamino)-2-propanol and 125 grams of 1,4-dichloro-2-butene (5% cis, 95% trans) and 29 grams of triethanolamine (0.2 mole) and 600 grams of water were mixed while heated on a steam bath to 80°–90° C., and kept at that temperature for 6 hours with constant stirring. Analysis of the viscous liquid product for ionic chloride indicated that the reaction was about 98% complete. It contained about 33% of active solids. Half of the product was subjected to steam destillation for the purpose of removing any unreacted monomers or other violate matter, but the residue appeared to be identical to the undistilled portion.

The product of this reaction appeared to be indistinguishable from the products of examples 12 and 13.

EXAMPLE 18

The procedure of Example 17 was repeated, except that the 1,4-dichloro-2-butene used was a mixture of 30% cis and 70% trans. The product appeared to be indistinguishable from the product of Examples 12, 13 and 17.

EXAMPLE 19

The procedure of Example 18 was repeated, except that the monoamine used was trimethylamine, instead of triethanolamine. The product appeared to be indistinguishable from the product of Example 14.

EXAMPLE 20

The procedure of Example 18 was repeated except that the monoamine used was dodecyl dimethylamine.

EXAMPLE 21

The procedure of Example 18 was repeated, except that the monoamine used was N-methyl morpholine.

EXAMPLE 22

The procedure of Example 13 was repeated, except that the following ratios of diamine and monoamine were used in separate synthesis.
  (a) 1,4-bis-(dimethylamino)-2-butene, 0.94 moles; triethanolamine, 0.12 moles
  (b) 1,4-bis-(dimethylamino)-2-butene, 0.85 moles; triethanolamine, 0.30 moles

EXAMPLE 23

The procedure of Example 18 was repeated, except that the following ratios of diamine and monoamine were used in separate synthesis.
  (a) 1,3-bis-(dimethylamino)-2-propanol, 0.95 moles; triethanolamine, 0.1 mole
  (b) 1,3-bis-(dimethylamino)-2-propanol; 0.86 moles triethanolamine; 0.28 moles The polymers of the present invention are sufficiently soluble in water to be incorporated as components of many cosmetic systems, particularly hair care preparations. They can be formulated to be compatable with high concentrations of many surfactants ordinarily used in shampoos, rinses, and creams.

The present polymers, furthermore, are substantive to hair and they impart a smooth, soft feeling thereto. They also promote detangling and easy combing of hair by diminishing "drag".

But, equally as important as these desirable hair-care properties, there appears to be no noticable "buildup" of polymer on the hair after continued use, so there is no subsequent "flaking off". These surprising properties are even more noticable with the present polymers than with any other similar polymers.

The hair-care properties were determined by studying the effects of hair-care preparations containing these polymers on DeMeo hair tresses in a manner well known in the art.

With respect of hair-care properties, the "capped" polymers of the present invention were found to be superior to the "non-capped" polymers, although the latter compounds were equal to the performance of similar previously known polymers.

The four polymers which gave the best results on the DeMeo tresses were:

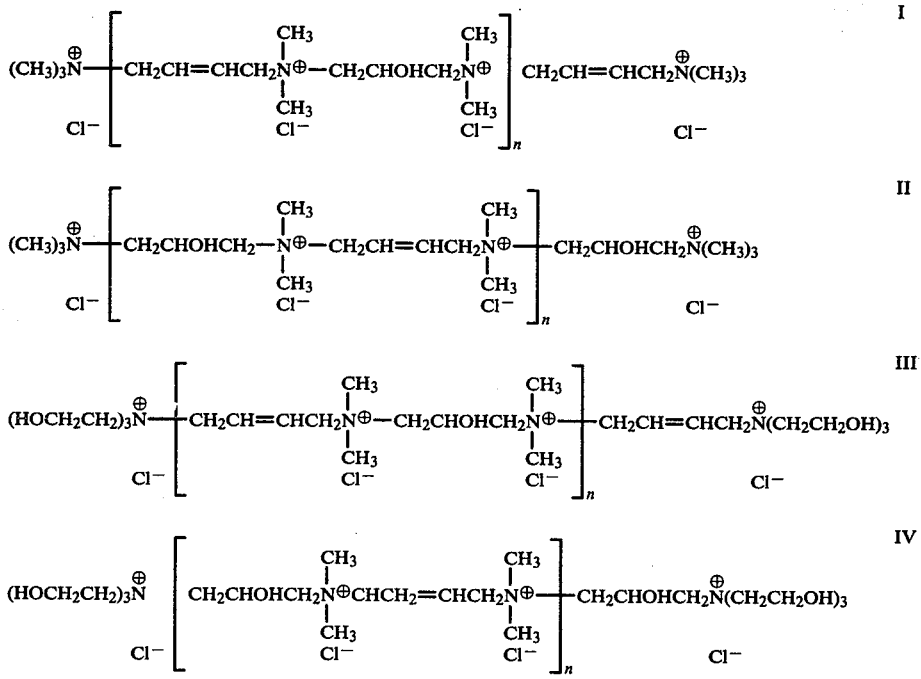

That is, polymers in which (I) R'=R''=—CH₃ and R'''=R^IV=R^V=—CH₂CH₂OH; and (II) R'=R''=—CH₃ and R'''=R^IV=R^V.

The bacterialogical properties of the compound of this invention were determined by performing simultaneous test with the most potent anti-microbial compound of the prior art namely,

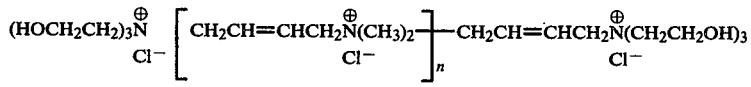

which was used as the control. The following procedure was used:

1. 50 ml. of germicide solutions of pre-selected concentrations were aspetically transferred to sterile 125 ml. flasks, then inoculated with 0.5 ml. of 1/10 nutrient broth culture of (a) *pseudonomas aeruginosa* and/or (b) *aerobactor aerogenes.*

2. Simultaneously, as controls, identical concentrations of the most active anti-microbial compound of the prior art were transferred to sterile flasks and similarly inoculated.

3. At 30 or 60 minute intervals following inoculation, aliquot portions of each germicide-organism mixture were plated in Tryptone Glucose Extract agar and inoculated at 37° C. for 48 hours.

4. The plates were read to determine the numbers of surviving ORGANISMS.

5. The results at each concentration of compound were compared with the control at the same concentration.

The compounds tested most thoroughly for bacteriological activity were the "capped" polymers in which
 (I) R'=R''=CH₃ and R'''=R^IV=R^V=—CH₂CH₂OH and
 (II) R'=R''=R'''=R^IV=R^V=—CH₃

In each instance, regardless of the cis:trans ratio, the monomers used to prepare the polymer, the ratio of bis-amine to mono-amine, and the particular organism used, each of these new compounds had bacteriological activity which was at least equal to that of the control. The uncapped polymer in which R^I=R^II=—CH₃, and the capped polymers in which R^I=R^II=—CH₃ and R^III=R^IV=R^V=—CH₂CH₂OH or —CH₃, were tested for their flocculant properties in water treatment by using the method described in U.S. Pat. No. 4,190,644.

All three polymers produced flocs at a concentration of about 10 parts per million. Their effectiveness was the same with the two cis:trans ratios that were tested.

The invention claimed is:

1. A method of conditioning the hair which comprises applying a hair conditioning effective amount to the hair of a compound or mixture of compounds having the structure:

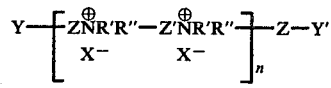

wherein (I)R' and R'' may be the same of different alkyl groups of from 1 to 18 carbon atoms, optionally substituted by from 1 to 2 hydroxyl groups or, (II) when taken together, will form a saturated or unsaturated ring of from 5 to 7 atoms, or (III) when taken together with N and an oxygen atom form the N-morpholino group; wherein Z is —CH₂CH═CHCH₂— when Z' is —CH₂CHOHCH₂— or Z is —CH₂CHOHCH₂— when Z' is —CH₂CH═CHCH₂—; wherein X is a halogen of atomic weight greater than 30; wherein Y and Y' may be either the same or different and may be either X or —NR'R"; and wherein n is an integer of from 2 to 20.

2. A method of conditioning the hair which comprises applying a hair conditioning effective amount to the hair of a compound or mixture of compounds characterized by the formula:

wherein (I), R' and R" are the same or different alkyl groups of from 1 to 18 carbon atoms optionally substituted by from 1 to 2 hydroxyl groups or (II) R' and R" together with N from a 5 to 7 membered N-heterocyclic ring, or (III) R' and R" together with N and an oxygen atom form a N-morpholino group; and wherein (I) R''' $R^{IV}$ and $R^V$ may be the same or different alkyl groups of from 1 to 18 carbon atoms optionally substituted by from 1 to 2 hydroxyl groups, or (II) R''' is a lower alkyl group of from 1 to 4 carbon atoms and $R^{IV}$ and $R^V$ taken together with N represent a 5 to 7 membered heterocyclic ring; or (III) R''' is a lower alkyl group of from 1 to 4 carbon atoms and $R^{IV}$ and $R^V$ taken together with N and an oxygen atom represent the N-morpholino group; n is an integer of from 2 to 20; and X is a halogen atom of an atomic weight greater than 30.

3. A method of conditioning the hair which comprises applying a hair conditioning effective amount to the hair of a compound or mixture of compounds characterized by the formula:

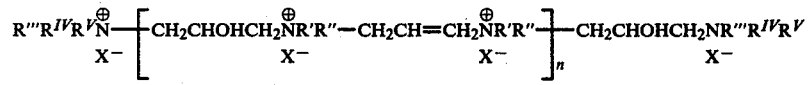

wherein (I), R' and R" are the same or different alkyl groups of from 1 to 18 carbon atoms optionally substituted by from 1 to 2 hydroxyl groups or (II) R' and R" together with N form a 5 to 7 membered N-heterocyclic ring, or (III) R' and R" together with N and an oxygen atom form a N-morpholino group; and wherein (I) R''', $R^{IV}$ and $R^V$ may be the same or different alkyl groups of from 1 to 18 carbon atoms optionally substituted by from 1 to 2 hydroxyl groups, or (II) R''' is a lower alkyl group of from 1 to 4 carbon atoms and $R^{IV}$ and $R^V$ taken together with N represent a 5 to 7 membered heterocyclic ring; or (III) R''' is a lower alkyl group of from 1 to 4 carbon atoms and $R^{IV}$ and $R^V$ taken together with N and an oxygen atom represent the N-morpholino group; n is an integer of from 2 to 20 and X is a halogen atom of an atomic weight greater than 30.

4. The method of claim 1 wherein the compound or mixture of compounds comprises a viscous solution containing 30 to 50% active solids and the solvent is selected from the group consisting of water, alcohol and mixtures thereof.

5. The method of claim 1 wherein the compound or mixture of compounds comprises a solid.

6. The method of claim 2 wherein the compound or mixture of compounds comprises a viscous solution containing 30 to 50% active solids and the solvent is selected from the group consisting of water, alcohol and mixtures thereof.

7. The method of claim 2 wherein the compound or mixture of compounds comprises a solid.

8. The method of claim 3 wherein the compound or mixture of compounds comprises a viscous solution containing 30 to 50% active solids and the solvent is selected from the group consisting of water, alcohol and mixtures thereof.

9. The method of claim 3 wherein the compound or mixture of compounds comprises a solid.

* * * * *